United States Patent [19]

Ricci et al.

[11] Patent Number: 5,043,440
[45] Date of Patent: Aug. 27, 1991

[54] OXIDATION PROCESS FOR PREPARING 4-ACYLOXY AZETIDINONES IN A TWO-PHASE SYSTEM

[75] Inventors: Marco Ricci; Maria Altamura, both of Novara; Daniele Bianchi, Milan; Walter Cabri, Limbiate; Norberto Gatti, Galliate, all of Italy

[73] Assignee: Farmitalia Carlo Erba S.p.A., Milan, Italy

[21] Appl. No.: 107,050

[22] Filed: Oct. 13, 1987

[30] Foreign Application Priority Data

Oct. 15, 1986 [IT] Italy ................................. 22003 A/86

[51] Int. Cl.$^5$ ..................... C07B 41/12; C07D 205/08
[52] U.S. Cl. .................................................. 540/357
[58] Field of Search ......................................... 540/357

[56] References Cited

U.S. PATENT DOCUMENTS 4,882,429 11/1989 McCombie ......................... 540/357

FOREIGN PATENT DOCUMENTS 180252    5/1986  European Pat. Off. .
0181831   5/1986  European Pat. Off. .
221846    5/1987  European Pat. Off. ............ 540/357
2144419   3/1985  United Kingdom ................. 540/357

OTHER PUBLICATIONS

Hanession, J. A., C.S. 107, 1438 (1985).
Sankyo, *Chemical Abstracts*, vol. 103, 123272t (1985).
Chackalamannil, *J. Org. Chem.*, 53, 450-452 (1988).
Shiozaki, *Tetrahedron*, 39, 2399-2407 (1983).

*Primary Examiner*—Mark L. Berch

*Attorney, Agent, or Firm*—Oblon, Spivak, McClelland, Maier & Neustadt

[57] ABSTRACT

Process for preparing compounds according to formula (I)

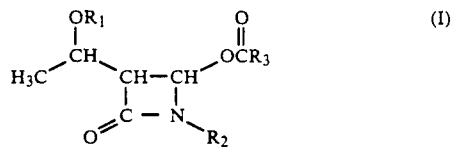

wherein $R_1$ and $R_2$ represent a hydrogen atom or a protective group and $R_3$ represents a $C_1$-$C_{10}$ alkyl or an aryl group, by oxidation of compounds according to formula (II)

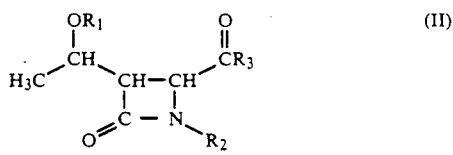

wherein $R_1$, $R_2$ and $R_3$ have the above-mentioned meanings, in a two-phase system comprising:
  a) an organic phase including a 4-acylazetidinone compound (II) and an "onium" salt dissolved in a medium immiscible with water,
  b) an aqueous solution including an alkali or alkaline-earth metal salt of an organic or inorganic peracid.

4-Acyloxyazetidinones (I) are useful intermediates in the synthesis of anti-bacterial compounds.

11 Claims, No Drawings

OXIDATION PROCESS FOR PREPARING 4-ACYLOXY AZETIDINONES IN A TWO-PHASE SYSTEM

4-Acyloxyazetidinones of formula (I)

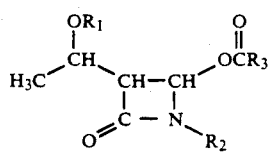

wherein $R_1$ and $R_2$ represent hydrogen atoms or groups protecting the alcoholic and amidic functions and $R_3$ represents a $C_1$-$C_{10}$ alkyl or an aryl group, are usually prepared by oxidation of the corresponding 4-acylazetidinones of formula (II)

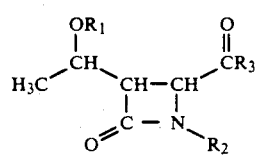

wherein $R_1$, $R_2$ and $R_3$ are defined as above; the above-mentioned reaction is known, as described, e.g., in S. Hanessian et al. *J. Am. Chem. Joc.*, 107, 1438(1485)

The resulting compounds of formula (I) are useful intermediates in the preparation of anti-bacterial compounds, called penems, as described, e.g., in U.K. Patent No. 2,111,496-B.

Said oxidation is carried out by means of organic peracids, such as e.g., monoperphthalic or m-chloroperbenzoic acid.

However, such reagents, even through only weakly acid by themselves, in consequence of their reduction give rise to the corresponding carboxylic acids with characteristic, relatively high, acidity constants. Consequently, the organic peracids, as such, do not allow satisfying results to be obtained in the oxidation of compounds, which are particularly unstable under acidic conditions, such as, e.g., the 4-acylazetidinones (II), wherein $R_1$ represents a hydrogen atom. The alcoholic function needs therefore to be protected by a group having a good stability in an acidic environment: to this end being usually employed the ter-butyldimethylsilyl group (see, M. Shiozaky, N. Ishida, H. Maruyama, T. Hirahoka, Tetrahedron 1983, 39, 2399; H. Maruyama, M. Shiozaky, T. Hirahoka, Bull. Chem. Soc. Jpn. 1985, 58, 3264; T. Chiba, T. Nakai, Chem. Lett. 1985, 651). However, owing to the high costs of the above-mentioned silyl group and of tetrabutylammonium chloride, which has to be employed for restoring afterwards the alcoholic function, said protective step represents a severe drawback in the industrial preparation of the anti-bacterial compounds to be obtained from the intermediate of formula (I).

Potassium peroxymonosulfate too has been at times employed in the oxidation of ketones to eters, but this compound, usually employed in mixture with acids such as KHSO or even sulfuric acid, is therefore barely effective towards substrates which are unstable under acidic conditions.

The object of the present invention is therefore to provide a easy and cheap method for oxidizing 4-acylazetidinones (II) to 4-acyloxyazetidinones (I), such method being capable to be applied to substrates with a non-protected alcoholic function.

Another object is to provide a method free from the corrosion and safely problems, which are generally encountered when organic peracid solutions are employed.

It has now been found that these and other objects are achieved by a process for preparing 4-acyloxyazetidinones of formula (I)

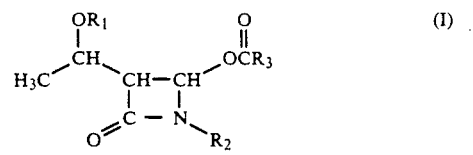

wherein $R_1$ represents a hydrogen atom or a group protecting the alcholic function, $R_2$ represents a hydrogen atom or a group protecting the amidic NH group and $R_3$ represents a $C_1$-$C_{10}$ alkyl or an aryl group, which consists of the oxidation of the corresponding 4-acylazetidinones of formula (II).

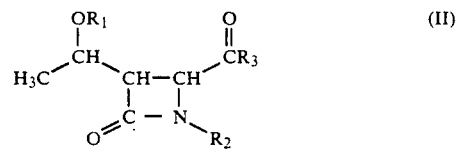

wherein $R_1$, $R_2$ and $R_3$ have the above-mentioned meanings, in a two-phase system comprising:
a) an organic phase including a 4-acylazetidinone (II) and an onium salt dissolved in a medium immiscible with water, and
b) an aqueous solution including an alkali or alkaline-earth metal salt of an organic or inorganic peracid.

Illustrative 4-acylazetidinones (II) which can be oxidized according to the present invention are those wherein $R_1$ represents a hydrogen atom or a silyl group (e.g., trimethylsilyl, and also ter-butyldimethylsilyl group), $R_2$ represents a hydrogen atom, a non-substituted or substituted benzyl group (e.g., p-methoxybenzyl) or a non-substituted or substituted phenyl group (e.g., p-methoxyphenyl) and $R_3$ represents a phenyl or alkyl group (e.g., methyl).

The raw materials according to formula (II) are known compounds or can be prepared using methods described in the literature, such as the above-metnioned papers and patents.

The general formula (I) encompasses all the optical forms (racemic or optically active). The preferred configurations are 3S, 4R for azetidinone and R for the carbon atom in the chain carrying the hydroxy group, so that the penem compounds resulting from the compounds of formula (I) have the final, preferred stereochemistry [5R,6S, (1R)].

In the reaction it can be employed, as onium salt, a quaternary ammonium or phosphonium salt according to formula (III).

$$(R_4R_5R_6R_7)M^+Y^-  \qquad (III)$$

wherein M represents a nitrogen or phosphorus atoms, $Y^-$ represents an inorganic stable anion such as $Cl^-$ or $HSO_4^-$ and $R_4$, $R_5$, $R_6$ and $R_7$ which can be the same or different, represent hydrocarbyl groups with a total content of carbon atoms between about 10 and 70.

Illustrative onium salts, which can be advantageously employed in the reaction, are dimethyl [dioctadecyl (75%)+ dihexadecyl (25%)] ammonium chloride (marketed as ARQUAD 2HT) and methyltrioctylammonium chloride (marketed as ALIQUAT 336).

As solvent, a solvent immiscible with water, such as ethyl acetate or chloroform, can be employed. As oxidizing agent, it can be employed in the reaction any alkali or alkaline-earth metal salt of any organic or inorganic peracid.

However, in view of their stability and large awailability on the market at moderate prices, potassium peroxy monosulfate and acid magnesium monoperoxy phthalate hexahydrate, marketed as H-48 are particularly attractive.

The reaction is carried out by vigorously stirring the two-phase mixture at temperatures between about 5° and 60° C., preferably between 15° and 45° C. The concentration of 4-acylazetidinone (II) in the organic phase can range between about 2 and 25% by weigh. The concentration of the peroxy compound in the aqueous phase, on the other hand, can range between about 2 and 15% by weight, its amount being in the range between about 1 and 5 moles per mole of 4-acylazetidinone (II). The onium salt is employed in amounts ranging between about 0.01 and 0.1 moles per mole of 4-acylazetidinone (II). The acidity of the solution can be further controlled by having the peroxy compound dissolved not in water, but in a buffer solution such as, e.g., a sodium phosphate solution at pH near 7. The duration of the reaction can range between about 5 and 48 hours depending on the selected conditions and, at the end of this period, 4-acyloxyazetidinone (I) is isolated according to conventional techniques.

The invention will be further illustrated by the following Examples, which are to be considered as merely illustrative and not limitative (yields are referred to products affording a single spot by their layer chromatography using silica gel layers Merck F-254 and, as eluant, ethyl acetate heptane 9/1; detection by irradiation with UV light at 254 nm).

EXAMPLE 1

In a two-necked, 50 ml, flask, provided with thermometer, reflux condenser and magnetic stirrer, 440 mg of (3S, 4S)-4-benzoyl-3-[(1R)-hydroxyethyl]-azetidine-2-one (2 mmoles), 3.5 ml of ethyl acetate, 50 mg of dimethyl [dioctadecyl (75%)+dihexadecyl (25%)] ammonium chloride (about 0.1 mmoles), 14 ml of Na phosphate buffer at pH 6.6 and 1.47 g of CAROAT$^{200}$, mixture containing 41.5% of potassium peroxymonosulfate (4 mmoles) as well as $KHSO_4$ and $K_2SO_4$, are charged. The mixture is heated, under vigorous stirring, to 40° C. and held at this temperature for 9 hours. At the end of this period the two phases are separated and the organic phase is washed with saturated bicarbonate solution and brine, dried over anhydrous sodium sulfate, filtered and evaporated. 310 mg of a yellowish solid are thus obtained which, after being washed with pentane, give 273 mg of (3R, 4R)-4-benzoyloxy-3-[(1R)-hydroxyethyl]-azetidine-2-one (yield: 58%), m.p.: 149°-151° C. [Crystals from ethylacetate/pentane]; $[\alpha]_D = +101°$ [c=1, methanol]; $^1$H-NMR (CDCl$_3$, 300 MHz); $\delta = 1.38$ (3H, d); 3.11 (1H, br); 3.39 (1H, dd, J=1.1 and 6.5 Hz); 4.28 (1H, m); 6.11 (1H, d, J=1.1 Hz); 7.17 (1H, br); 7.47, 7.62 and 8.05 (5H, mmm); M.S. (C.I. isobutane): m/e=235 (M+).

EXAMPLE 2

The example 1 has been repeated replacing CAROAT® by 1.98 g of acid magnesium monoperoxyphtalate hexahydrate (H-48; 4 mmoles), employing 20 ml of Na phosphate buffer at pH 6.6 and extending the reaction time to 10 hours.

264 mg of (3R, 4R)-4-benzoyloxy-3-[(1R)-hydroxyethyl]-azetidine-2-one (yield: 56%) are thus obtained.

EXAMPLE 3 (COMPARATIVE)

In a two-necked, 50 ml, flask, provided with thermometer, reflux condenser and magnetic stirrer, 440 mg of (3S, 4S)-4-benzoyl-3-[(1R)-hydroxyethyl]-azetidine-2-one (2 mmoles), 10 ml of chloroform and 1,53 g of 90% m-chloro perbenzoic acid (8 mmoles) are charged and the resulting solution is stirred for 60 hours at room temperature. At the end of this period, the solution is washed with saturated aqueous solutions of sodium meta-bisulfite, sodium bicarbonate and sodium chloride, dried over anhydrous calcium chloride, filtered and evaporated. 180 mg of pure (3R, 4R)-4-benzoyloxy-3-[(1R)-hydroxyethyl]-azetidine-2-one (yield:38%) are thus obtained.

We claim:

1. A process for preparing compounds of formula (I):

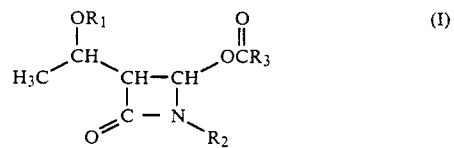

wherein $R_1$ is a hydrogen atom or an alkylsilyl hydroxy protecting group, $R_2$ is a hydrogen atom or a substituted or unsubstituted benzyl or a substituted or unsubstituted phenyl amidic NH protecting group, and $R_3$ is a $C_1$-$C_{10}$ alkyl or an aryl group, said process comprising the step of: (i) oxidizing a compound of formula (II)

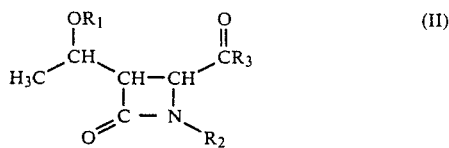

wherein $R_1$, $R_2$, and $R_3$ have the above-mentioned meanings, in a two-phase system comprising:
  a) an organic phase comprising a compound of formula (II) and an onium salt dissolved in a solvent immiscible with water; and
  b) an aqueous phase comprising an alkali or alkaline-earth metal salt of an organic or inorganic peracid.

2. The process according to claim 1, wherein $R_1$ is a hydrogen atom, $R_2$ is a hydrogen atom, and $R_3$ is a $C_1$-$C_{10}$ alkyl or phenyl group.

3. The process according to claim 1, wherein said onium salt is a quaternary ammonium or phosphonium salt of formula (III)

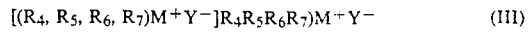

wherein M is nitrogen or phosphorus, Y− is a stable inorganic anion and $R_4$, $R_5$, $R_6$ and $R_7$ are the same or different and are hydrocarbyl groups with a total content of carbon atoms between 10 and 70.

4. The process according to claim 3, wherein said onium salt is dimethyl/dioctadecyl (75%)+dihexadecyl (25%) /ammonium chloride or methyltrioctylammonium chloride.

5. The process according to claim 1, wherein said solvent immiscible with water is ethyl acetate or chloroform.

6. The process according to claim 1, wherein said alkali or alkaline-earth metal salt of said peracid is potassium peroxy-monosulfate or acid magnesium monoperoxyphthalate hexahydrate.

7. The process according to claim 1, wherein said oxidizing step is carried out at a temperature between 5° and 60° C. for a period of time in the range between about 5 and 48 hours.

8. The process according to claim 1, wherein the concentration of said compound of formula (II) in said organic phase is between about 2 and 25% by weight, the concentration of said salt of said organic or inorganic peracid in said aqueous phase is between 2 and 15%, and the amount of said salt of said organic or inorganic peracid is between about 1 and 5 moles per mole of said compound of formula (II), and said onium salt is employed in an amount ranging between about 0.01 and 0.1 moles per mole of said compound of formula (II).

9. The process according to claim 1, wherein the pH of said aqueous phase is controlled by a buffer.

10. The process according to claim 9, wherein said buffer is a sodium phosphate solution with pH near 7.

11. The process according to claim 7, wherein said temperature is between 15° and 45° C.

* * * * *